(12) United States Patent
Aghili et al.

(10) Patent No.: US 7,233,906 B1
(45) Date of Patent: Jun. 19, 2007

(54) PROGRESS NOTES MODEL IN A CLINICAL INFORMATION SYSTEM

(75) Inventors: Houtan Aghili, Somers, NY (US); Richard A. Mushlin, Ridgefield, CT (US); Jeffrey S. Rose, Greenwood Village, CO (US); Rose Williams, Glenham, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 09/479,259

(22) Filed: Jan. 7, 2000

Related U.S. Application Data

(63) Continuation of application No. 09/031,198, filed on Feb. 26, 1998, now Pat. No. 6,289,316.

(60) Provisional application No. 60/041,199, filed on Mar. 25, 1997.

(51) Int. Cl.
*G06Q 30/00* (2006.01)

(52) U.S. Cl. .............................. 705/3; 705/2; 707/104.1

(58) Field of Classification Search .................... 705/2, 705/3; 707/104.1, 102; 345/846, 853; 600/301
See application file for complete search history.

(56) References Cited

U.S. PATENT DOCUMENTS

| | | | |
|---|---|---|---|
| 4,878,175 A | * | 10/1989 | Norden-Paul et al. ......... 705/2 |
| 5,077,666 A | * | 12/1991 | Brimm et al. .................. 705/2 |
| 5,265,010 A | * | 11/1993 | Evans-Paganelli et al. |
| 5,794,208 A | * | 8/1998 | Goltra ............................ 705/3 |
| 5,802,495 A | * | 9/1998 | Goltra ............................ 705/3 |
| 5,812,984 A | * | 9/1998 | Goltra ............................ 705/3 |
| 5,850,221 A | * | 12/1998 | Macrae et al. .............. 345/348 |
| 5,924,074 A | * | 7/1999 | Evans ......................... 705/2 X |
| 5,946,659 A | * | 8/1999 | Lancelot et al. ............ 705/2 X |
| 6,192,345 B1 | * | 2/2001 | Chicorel ........................ 703/3 |

FOREIGN PATENT DOCUMENTS

JP        407056989 A    *   3/1995

OTHER PUBLICATIONS

Ornstein et al. "The computer-Based Medical Record: Current Status" JHournal of Family Practice, v. 35, n .5, p. 556(10), Nov. 1992.*

Aghili et al. "Progress Notes Model" AMIA 1997 Annual Fall Symposium paper Session S2, Oct. 27, 1997.*

* cited by examiner

*Primary Examiner*—Raquel Alvarez
(74) *Attorney, Agent, or Firm*—Satheesh Kara; Greenblum & Bernstein P.L.C.

(57) ABSTRACT

A progress note in a patient's medical record can be created in a database format which is unalterable. New versions of the notes which reflect revised viewpoints of the user may be created without deleting original notes. The database which stores these progress notes can check accuracy in diagnosis and orders by the user.

5 Claims, 10 Drawing Sheets

FIG.10

CIS Desktop William, Rose (900012) MD
Progress Notes for: SMITH, ADA (002105355), F, 05-01-1919, H: 755-1621

File  Edit  Subjective  Objective  Assessment  Plan  Signature  View  Help

*01-09-1997

Site of Care: EAST CLINIC/INTERNAL MEDICINE

P    Chronic olitus media.
     Lab ⟶ 701
     CBC -nl (01-10-97)
     Throat culture
     Medication ⟶ 703
     Sudafed 60 mg. sig: one table
     q 6 hours
     Amoxicillin 500 mg. sig: TID x 14 days S    Sore Throat ⟶ 705

O    Vital Sign ⟶ 707
     Reminder

A    Acute Strep Throat ⟶ 709

P    Amoxicillin 500 mg ⟶ 711

PROGRESS NOTES MODEL IN A CLINICAL INFORMATION SYSTEM

CROSS-REFERENCE TO RELATED APPLICATION

This application is a continuation of U.S. application Ser. No. 09/031,198, filed on Feb. 26, 1998, now U.S. Pat. No. 6,289,316, which is a continuation-in-part (CIP) of U.S. Provisional Application 60/041,199 filed on Mar. 25, 1997, both of which are herein incorporated by reference.

BACKGROUND OF THE INVENTION

1. Field of the Invention

The present invention generally relates to Clinical Information Systems (CIS) and, more particularly, to computer implementation of Progress Notes (PNs) in an electronic patient chart.

2. Background Description

A patient's medical chart is a complex collection of all the relevant "facts" relating to the patient's health. This raw data can be quite voluminous, and this has led to efforts to manage the data with a computer rather than with paper. But just keeping track of the data is not enough, to be useful and illuminating to the health care professional, the data must be organized in familiar and predictable ways.

There is no universal standard for the organization of a medical chart, be it paper or electronic. However, certain paradigms have evolved in modern medical practice using the paper chart. These can serve as the starting point for the level of standardization which the computerized patient record demands. Two organizing principles stand out as useful approaches for making patient data more informative: clinical histories and Progress Notes (PNs).

"Clinical Histories" denote the grouping of patient data by its type, independent of the context in which the data was recorded. Refinements can include further sub-classification and sorting. For example, a medication history includes all medication data, but not laboratory data, even though certain medications may have been prescribed based on the results of certain laboratory tests. The medication history may be grouped by drug and sorted by date to make it more readable. Observe that it is only because the reader associates certain drugs with certain medical conditions that the medication history is useful for understanding the patient's problems and treatment. When several histories are considered together (e.g., medications, laboratory tests, procedures, family history, allergies), the experienced clinician can piece together a more complete picture of the patient's condition. The completeness of the record and the skill of the clinician combine to make the historical, data-centered view of the chart a useful clinical tool.

But the clinicians, and the health care enterprise, want more information. They want the context in which the data was generated. This context includes the relationships between medical facts and the thought processes involved in investigating, diagnosing, and treating medical conditions. The "Progress Note" or PN is the vehicle for capturing that context. In practice, the degree of structure evident in Progress Notes spans the continuum from unstructured stream-of-consciousness text, to highly structured machine-readable forms. Although most Progress Notes exhibit neither of these extremes, the reason for the polarization is clear: the content must be both expressive and searchable. A common approach is to record information as labeled, stylized, free text, optimized for visual scanning by clinicians, in one place, and selectively code certain information, optimized for processing by data analysts, in another place. With this scheme, neither the clinician nor the analyst has easy access to the complete picture.

SUMMARY OF THE INVENTION

It is therefore an object of the present invention to provide computer implemented method for generating and storing a medical chart which is expressive, searchable, and facilitates both data-centered (historical) and process-centered (contextual) views.

According to the invention, there is provided a computer implemented method for generating Progress Notes (PNs) in a Clinical Information System (CIS). The Progress Notes function of this invention is designed around the following key points:

1. All medical data entered into the chart should be part of a Progress Note, independent of their use elsewhere in the chart. The intent is to always preserve the context in which events occur.
2. Progress Notes should support both business and clinical analysis by storing data in coded form, while providing medically familiar textual documentation.
3. Progress Notes should allow for entries by multiple authors without sacrificing individual accountability. This behavior should support both the common physician/nurse office visit scenario as well as the broader team approach to treatment.
4. Progress Notes should allow useful documentation patterns to be captured and later applied, with suitable modification, in similar clinical situations. The goal is to facilitate ease of use, reduce time spent entering data, and provide a framework for protocol definition and management.

The model implemented by the invention addresses each of these points. The following description of the preferred embodiment of the invention defines layers of data organization used for Progress Notes (PNs), exposes the structure of the principle PN components and describes their behavior within, and effect on, the PN. The Progress Notes as implemented by the invention are readable, easily understood, complete, accurate and concise. They are also flexible enough to logically convey to others what happened during an encounter, e.g., the chain of events during the visit, as well as guaranteeing full accountability for documented material, e.g., who recorded the information and when it was recorded.

BRIEF DESCRIPTION OF THE DRAWINGS

The foregoing and other objects, aspects and advantages will be better understood from the following detailed description of a preferred embodiment of the invention with reference to the drawings, in which:

FIG. 10 is a sample progress note as it would appear on a computer monitor.

DETAILED DESCRIPTION OF A PREFERRED EMBODIMENT OF THE INVENTION

Figure 1:
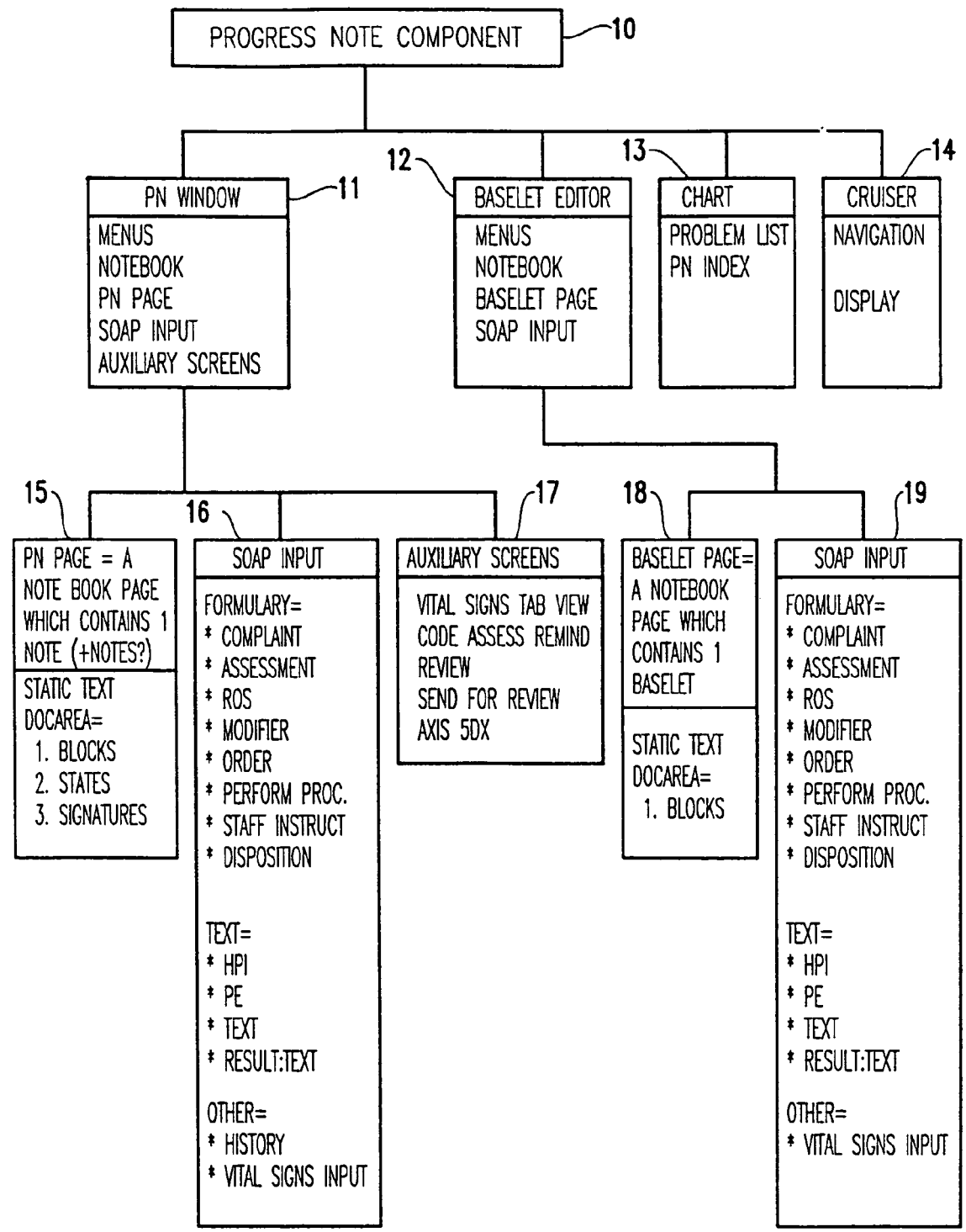
FIG. 1 is a block diagram showing the system architecture depicting the sub-components which collectively represent the PN component.

The computer implemented method of the present invention may be implemented on a variety of hardware platforms such as, for example, an IBM RS/6000 workstation running the application program embodying the method. Alternatively, the process may be implemented to run on a sixteen-way IBM SP2 machine. The SP2 machine is a collection IBM RS/6000 engines running under a common umbrella and the AIX operating system (IBM's version of the UNIX operating system) and connected with a high speed switch. It could also be implemented on other hardware platforms including, but not limited to, mini computers, stand alone UNIX or Windows NT workstations, or workstations in a network, or mainframes, including IBM AS400 and ES9000 computers.

A medical chart is both a transaction system and a documentation tool. Some information is purely descriptive, and the documentation serves to highlight the clinically relevant aspects of the state of the patient. Other data is proscriptive, and the documentation serves to initiate the transaction as well as provide a description for future reference. It is important to distinguish between the data and the documentation. For example, an order "happens to" the patient, and is presumably for the patient's benefit, while the documentation of that order in the note is primarily for the clinician. The details, which are most important for the correct execution of the order, are not necessarily the same as those which provide the most appropriate documentation.

In our model, the data itself is captured in a unit called an event. There are many types and subtypes of events, organized into a hierarchy whose "leaves" (terminal nodes) are used as the transaction units of the system. Examples are a chief complaint, a set of vital signs, a clinical pathology result, a diagnosis, a medication order, and a patient instruction. These data structures are optimized for transactions and histories. They contain coded elements, numerical values, text descriptions, and system identifiers. Patient, author, and time stamps are among the identifiers present in every event. In addition, every event is directly or indirectly (through another event) linked to one and only one Progress Note (PN).

When an event is documented in a PN, the event itself can provide information relevant for that purpose, including transformed or filtered information. For example, the code for a diagnosis is important in the transaction and search realms, but the name is the important documentation feature. By encapsulating functions which generate the descriptions of events, the invention assures consistency of documentation throughout the chart.

The documentation requirements for a Progress Note, however, exceed the encapsulated descriptions of the events alone. Progress Notes have evolved their own "look and feel", classifying and arranging information so that the reader can understand what the author was thinking. One common set of guidelines for Progress Note (PN) writing is the so-called "SOAP" model. In this idealized format, the author documents information relevant to the patient contact including the account of the illness by the patient (Subjective data), observations by the health care provider, such as vital signs and physical exam (Objective data), the reasoning behind a diagnosis and treatment plan (Assessment), and disposition instructions (the Plan). This structure of a Progress Note (PN) (introduced by Dr. Lawrence Weed, "The Problem Oriented Record as a Basic Tool in Medical Education, Patient Care, and Research", *Ann. Clin. Res.*, 1971, 3(3)) is widely recognized by most health care providers, and this invention generally follows this approach because it is organized, logical, familiar and essential for retrieving and evaluating information in the record. Although different general types of notes may be created (visit, telephone, advice, consultation, comment, summary) and different providers may input different kinds of data, the base organization into these four areas (SOAP) applies generally across all patient notes. This structured approach also creates a foundation for automated decision support and artificial intelligence (AI) and knowledge coupling applications in the future.

From an information model standpoint, the Progress Note (PN) can be best described as the logical integrator of clinical data relative to a health care contact. The PN should present a care giver with the full complement of diverse medical data relevant to a patient contact, whether that data has been obtained from the patient or gathered through observation or medical testing. An optimal PN should make it unnecessary to turn to any other portion of the chart to gather the facts about an encounter as they were perceived by the documentor of the care (e.g., physician or nurse, referred to herein as the care giver). The reader of the PN may wish to access other sections of the record to enrich or complete their understanding of the patient's overall medical conditions (e.g., the relationship of laboratory results in the note to those in other encounters) or to evaluate patterns which may be best detected when like types of data are reviewed categorically. Even in the case where such aggregate categories (laboratory results, allergies, hospitalizations, etc.) are reviewed outside the PN, the care giver may well document the results or conclusions from such surveys in the note so that others can follow their thought process in the future without having to guess at the elements that led to a particular conclusion.

In practice, the arrangement and appearance of the note can vary widely from the prototypical SOAP format, depending on the author's style, documentation goals, practice management guidelines, and the patient's condition. Therefore, structures which impose a fixed arrangement of S, O, A, and P elements are considered unusable. Equally unacceptable are structures which label every entry with a SOAP letter, but arrange the entries chronologically. The model used in the invention automatically labels the entries, but allows the author to insert the entries anywhere, subject to certain restrictions for enforcing accountability.

One important accountability issue is the handling of revisions to existing documentation. Our model deals with two kinds of revisions.

1. Recording errors, such as misspellings or entering "right" when the author means "left" are corrected by allowing the author to replace the information but with the original data accessible for audit.

2. An evolution or refinement of clinical judgment is different in that both the original as well as the revision are considered equally valid at the time they were entered. For example, an initial diagnosis of a sinus infection may be replaced with a diagnosis of migraine after further investigation.

The "story" that the note tells certainly depends on the relative positions of the two judgements. Again, accountability requires that the model embody certain limitations on the arrangement of entries in the note.

To handle the labeling, arrangement, and accountability requirements of the note, our model defines a structure called a "block" which serves as the atomic unit of the documentation. A block has access to the data stored in one or more events, maintains the correct labels for the data, maintains the correct position in the note, enforces limitations on rearrangement, maintains audit trails of in-place revisions, and constructs the appropriate documentation text to represent its underlying "event" data.

Both events and blocks are persistent in our model. The information relevant to transactions and histories is stored in events, while the information needed for Progress Notes documentation is stored in blocks, including an access path to associated events. This separation of function allows an application to change the "look and feel" of the Progress Note without affecting the transaction or history-building subsystems. This facilitates the integration of new event types and the retrofitting of our Progress Notes model to existing clinical repositories.

The Progress Note (PN) is modeled as a sequence of blocks. The order of the sequence is controlled by the authors and by the accountability model. Every block is assigned a chart-specific note identifier and a note-specific sequence position. Each event is assigned to one and only one block, but a given block may represent more than one event. This many-events-to-one-block relationship manages the "versions" used to correct recording errors.

This simple model of the Progress Note allows for a wide range of possibilities for authorship, appearance, and analysis. A noteworthy feature of our model is that notes have a well-defined beginning, when the first block is inserted, but no end. An author may add new information to an existing note, or start a new note, based on clinical judgement and practice guidelines, without artificial system limitations. This implies that a single PN can be used to document a part of an encounter, a whole encounter, multiple encounters, or entire episodes of care without having to strictly define "encounter" or "episode", for which there is not any standard universal meaning.

Traditional paper charts usually attempt to impose a notion of closure on documentation based on the encounter concept. The encounter boundaries, however, are often determined by financial practices rather than by clinical models. An advantage of our electronic chart is that financial information scan he obtained from the transaction record, while the documentation record can be better tailored for clinical use, without loss of data for either purpose.

The act of "signing" a Progress Note takes on a special meaning in an electronic chart. In constrast to a paper chart, the act of "signing" a Progress Note takes on a special meaning in an electronic chart. In a paper chart, signing (or sometimes initialing) imparts two distinct meanings in one act. Namely, 1. It serves as a means to "authenticate" the author.
2. It attests to the author's confidence that the signed portion reflects sound medical judgement.

In the electronic chart, the authentication task is accomplished automatically by the log-on procedure to the system. Every block, therefore, has a specific known author. Signature, then, takes on a pure accountability meaning, which is captured with two special blocks: Initial and Sign. Together, they address the need for expressiveness, which requires that the note allow for the free arrangement of blocks, and the need for accountability, which requires that the author be able to prevent rearrangement and insertion, which in turn might change the perceived meaning of the original documentation. In our model, initialing a note prevents rearrangement above the initialing point but allows insertion. Signing prevents both rearrangement and insertion above the signature. Correction of recording errors is always allowed for that block's author and never for another author, regardless of initial or signatures anywhere in the note. Accountability is therefore addressed by automatic identification, two levels of content locking, and controlled, traceable content versioning.

Our electronic chart takes advantage of the high degree of internal structure and content coding present in the notes by constructing a Progress Notes index. The index maintains attributes such as dates, diagnoses, authors, and procedures, extracted from all notes in the chart and organized into sortable, filterable, searchable structure. This structure serves the combined purpose of facilitating access to particular notes, white automatically maintaining a useful clinical summary, similar to the traditional "problem list".

Using the structure discussed above, together with collections of coded elements from controlled medical vocabularies, an author can construct Progress Notes to document a wide variety of clinical situations. It would be advantageous if common patterns of documentation could be captured, tailored, and reused within the health care enterprise. This would save time and effort, as well as allow both standardization and customization of protocols. To be useful, such a system would require the right balance between very specific "templates", from which the correct instance would have to be selected from a very large library, and a small number of general purpose "guidelines", each of which would need extensive tailoring on every use.

Our system provides an intermediate mechanism which allows progress notes to be written for a "virtual" patient, with two levels of customizability for application in specific clinical situations. We have coined the term "baselet" to describe a Progress Note in which coded elements from a "small view of the knowledge base" are pre-coordinated into a "living" documentation "template" ("baselet") with the desired degree of flexibility.

A baselet is a combination of "macro" and "menu" representations of blocks within a Progress Note. The application provides for an authoring mode in which baselet notes can be written exactly as the would be for "live" notes, with several special features:

The baselet is written outside the context of a patient chart and can be stored in a baselet library and retrieved for later editing.

None of the blocks are committed, which means no transactions are generated, even when the specification of an event is complete.

Checking for completeness of data entry is turned off which means events need not be completely specified.

Versions of events are not maintained, which means that editing a "baselet" block replaces its associated event.

The coded elements, which represent the clinical data, can be assigned attributes to control their behavior during the tailoring process when the baselet is applied to a live note. This facilitates capturing default and alternative choices, deferring the selection of the exact mix until the baselet is applied. Rare choices, not anticipated by the baselet author can be added by the user and seamlessly integrated with the current baselet.

Observe that the baselet notion offers significant advantages over the traditional notion of templates. Namely, 1. Templates have a "fixed" format. In order to serve a large user community with diverse needs, e.g., the various medical specialties, one has to design a huge number of templates. Baselets, on the other hand, do not have a fixed format, and can be extended or abbreviated from a standard "startup kit" by each author as needed, without loss of coded information.
2. Templates, having a fixed format, document all of the fields they contain when committed. This implies that for cases when a template is sparsely populated, the entire template is still recorded resulting in hard-to-read documentation. Baselets, on the other hand, only commit the blocks which the author determines to commit.
3. The authoring of templates is a separate and distinct process from their use. This results in having a group of template "designers," and another group of template "users." This separation of function makes it particularly difficult to introduce new recording patterns into practice. Baselets, in contrast, are authored in exactly the same way as notes. This enables an enterprise, or an individual author, to take an existing note and convert it to a baselet for future use. That is, as the use of the system evolves, and the "useful" patterns are identified, they will be captured and reused for better documentation of care.

With this introduction to the data structure of Progress Notes, reference is now made to FIG. 1 which shows the sub-components which collectively represent the Progress Note. The Progress Note (PN) component 10 comprises a PN Window 11, a Baselet Editor 12, a Chart 13, and a Cruiser 14. The PN Window 11 includes menus, a notebook composed of PN pages, a SOAP input and various auxiliary screens. In more detail, a PN page 15 is a notebook page containing one note in the form of static text comprised of blocks, states and signatures. A SOAP input 16 includes the formulary, text and other data. By "formulary" what is meant is the patient's complaint, the care giver's assessment, a review of system (ROS) data entry screen, modifiers for modifying a coded complaint or assessment, orders, performance procedure, staff instruction, and disposition. The auxiliary screens 17 include, for example, vital signs, coded assessment, and review. The Baselet Editor 12 is comprised of menus, a notebook composed of baselet pages and a SOAP input. The baselet page 18 is similar to the notebook page, and the SOAP input 19 is similar to the SOAP input 16. The Chart 13 is comprised of a problem list and a PN index. The Cruiser 14 is comprised of navigation and display components.

Figure 2:
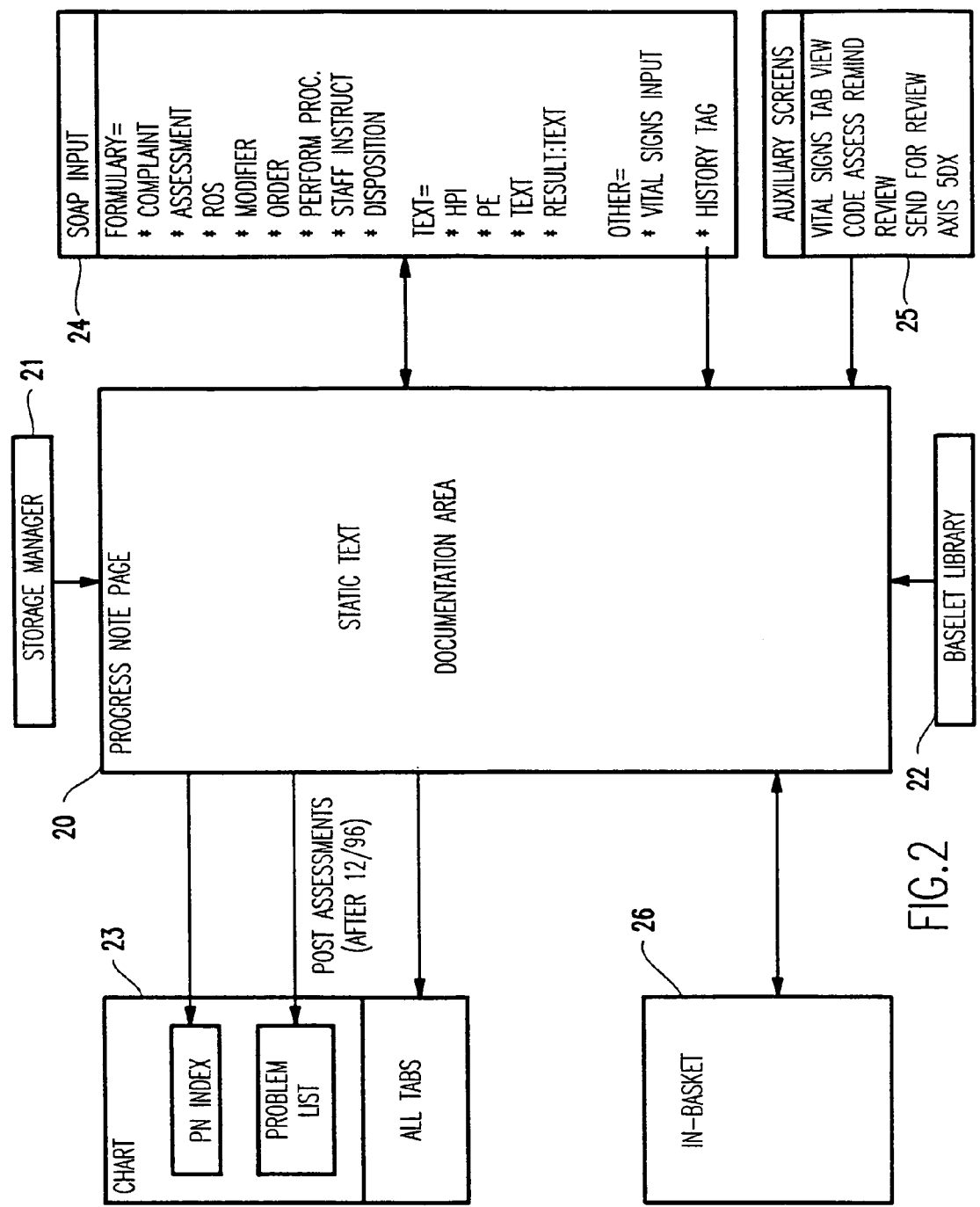
FIG. 2 is a block diagram showing the data flow between the system and a PN page.

The data flow for a Progress Note page is shown in FIG. 2, where the static text documentation area of the Progress Note page 20 receives input from a storage manager 21 and a baselet library 22. A Progress Note page is accessed by a PN index or a problem list in the chart 23. Input to the static text of the Progress Note page is via the SOAP input 24. Also, auxiliary screens 25 can be accessed from the Progress Note page, and an in-basket 26 can be used by the care giver to access the Progress Note page 20.

Figure 3:
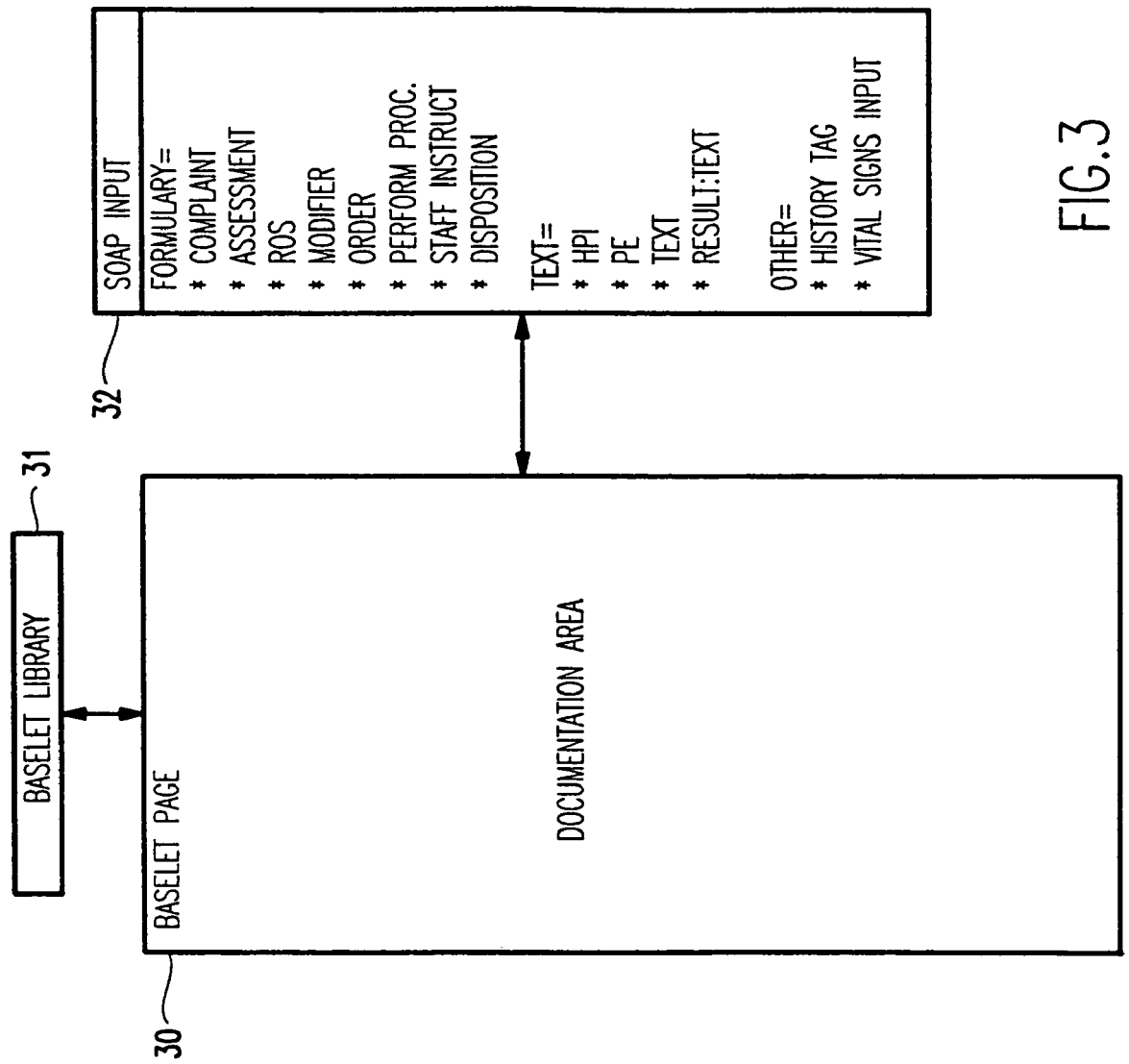
FIG. 3 is a block diagram showing the data flow between the system and the baselet editor.

The data flow for the baselet page is an abbreviated version of the data flow for the Progress Note page, as shown in FIG. 3. In this case, the baselet page 30 access the baselet library 31, and input to the documentation area if via the SOAP input 32.

Figure 4:
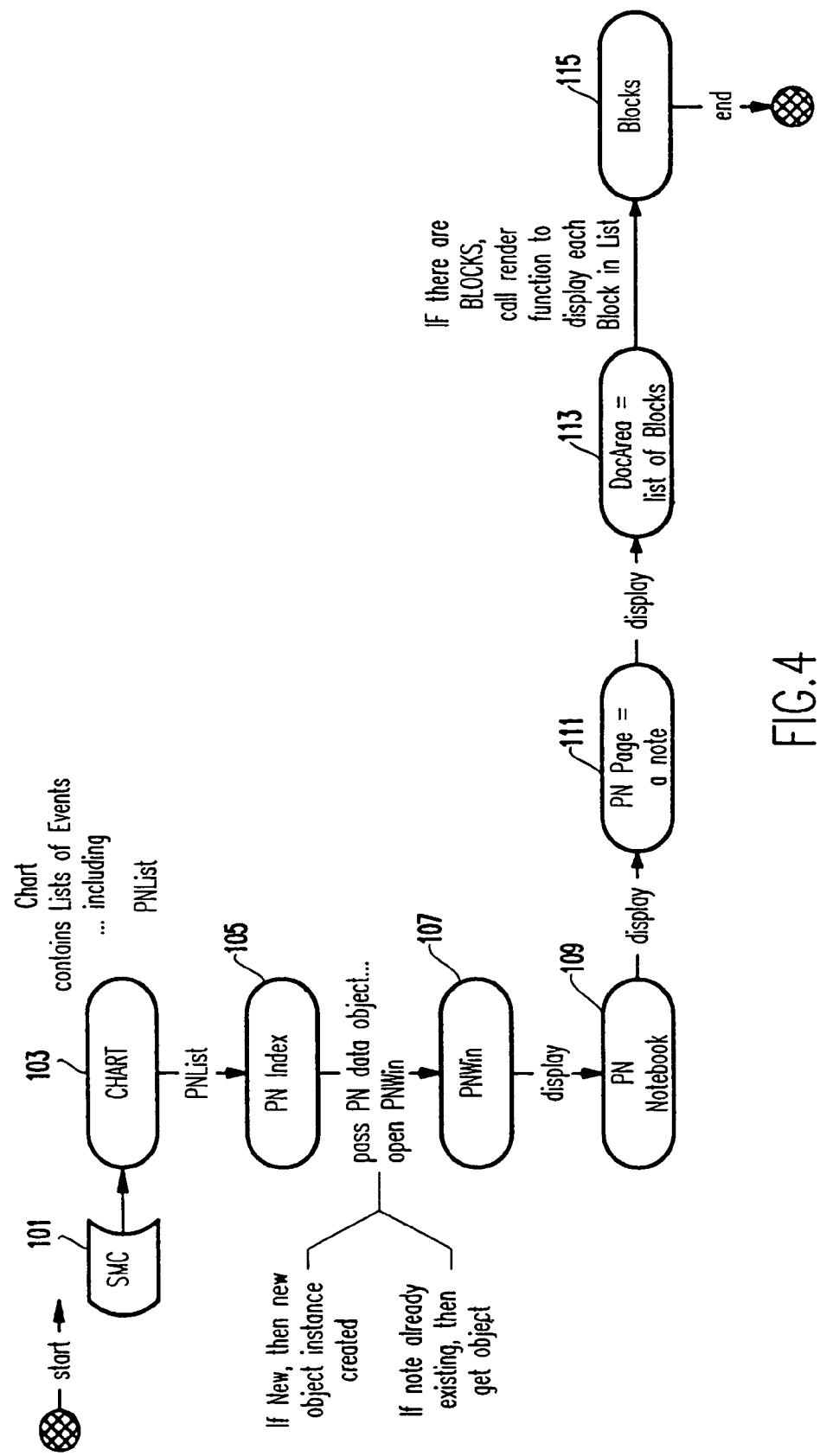
FIG. 4 is a flow chart of the overall computer implemented method illustrated by the steps for creating a new PN note.

The invention is best understood with reference to the flow charts shown in FIGS. 4 to 9. The patient record can be thought of as a "notebook" with tabs relating to various subject areas. FIG. 4 shows the steps of creating a new note in the "patient's notebook". A "storage-manager-client" or SMC database 101 is accessed to retrieve a chart in block 103. The chart contains, among other things, a PN list. The user is prompted in block 105 to choose from the PN index a PN data object. If the PN already exists, the PN data object is passed to open a Progress Note Window (PNWin) on a computer display in block 107. A new "notebook" for a new patient may be opened by creating an new object instance. This is done by choosing a blank chart which, when displayed, prompts the user to enter basic information about the patient, such as name, age, gender, identification (ID) number, and the like. The newly created PN data object is then passed to open the PN Window in block 107.

The PN data object is displayed as a PN Notebook in block 109. The PN Notebook comprises a plurality of pages, each page containing a note which may list, for example, dates of previous office visits and basic reasons for visits. It may also list the health provider seen by the patient. Therefore, the user pages to a page in the PN Notebook in block 111. A blank entry is displayed for new visits. This entry may be set to automatically display the current date. Next, as shown in block 113, blocks are created as part of the user data entry in the PN Notebook page. These blocks follow the standard method in which the medical community keeps patient records; i.e., the SOAP method. Therefore, there will be an "S" block for subjective information, an "O" block for objective data, an "A" block for assessment, and a "P" block for the treatment plan.

For each bock there are three methods of creating the record. First, the user may simply type in the text as in any standard wordprocessor format. A second entry method is for the user to select key phrases from a menu. The third entry method would be to follow a baselet format. Then, as shown in block 115 the blocks created are displayed.

Figure 5:
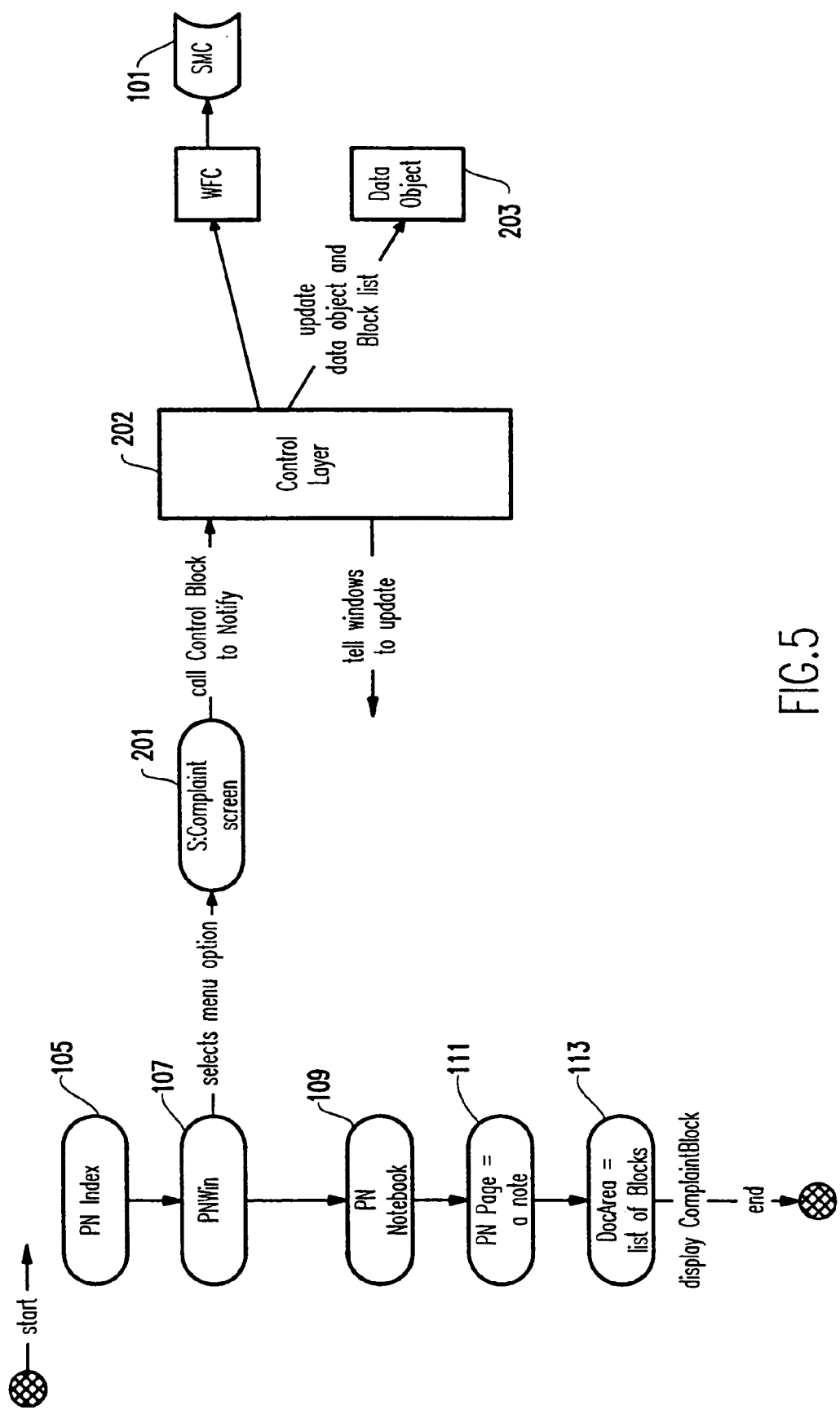
FIG. 5 is a flow chart, based on the flow chart of FIG. 1, showing the steps for creating a new complaint block.

FIG. 5 shows an example of a flow chart for creating a new "S" block, or the patient's complaint. In FIG. 5, and the figures which follow, identical reference numerals denote identical software components of the overall flow chart shown in FIG. 4. The steps shown in this flow chart would also apply to creation of "O" and "A" blocks. This process begins with the PN Window 107. The user is prompted to select a menu option and, in the example illustrated, the S:Complaint screen 201 is selected. Upon selection of this screen, the process calls the control layer 202. The control layer 202 verifies the information entered against system requirements. For instance, certain kinds of information may only be entered by specific users. The system will know, based on a password used to enter the database, whether or not the user is a medical doctor (M.D.), a registered nurse (R.N.), a nurse practitioner (N.P.), a physician's assistant (P.A.), the patient's treating physician, a consulting physician, etc. The control layer verifies that the person entering the information can enter the type of information to be entered. Some users may not be permitted to enter information in certain blocks (S, O, A, P). The system also accesses the SMC database 101 to check whether an order is contraindicated or a diagnosis is incorrect based on other patient data (other prescriptions the patient is taking, laboratory tests to be administered, or physical condition of the patient). From the control layer 202, the data object and block list 203 are updated and the PN is updated in the Progress Note notebook 109.

In the alternative, the SOAP information is not immediately stored in any individual patient medical chart in the CIS. The care giver is prompted to designate individual terms in the baselet as being in either a "positive", a "negative", or an "off" state. Then the baselet, with all its terms and term state information, is stored in the baselet library. The care giver can place a baselet in a Progress Note (PN) for a specific patient. To do this, the care giver responds to a prompt to apply to the PN in which the baselet has been place only those terms from the baselet which are in the "positive" and "negative" state. The care giver is then prompted to input additional data as required by any term thus added to the PN.

Figure 6:
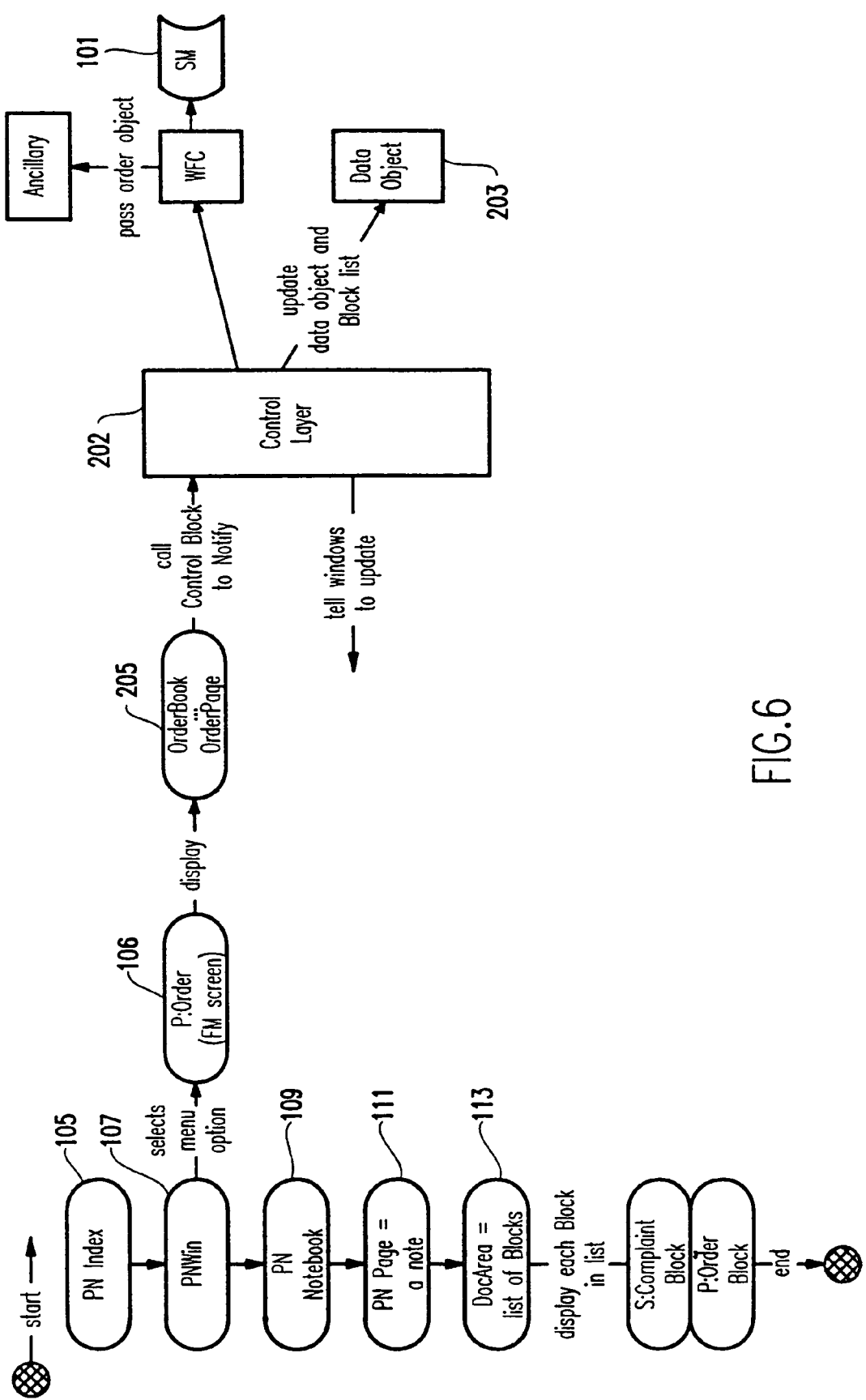
FIG. 6 is a flow chart; based on the flow chart of FIG. 1, showing the steps for creating an order block.

The steps for creating a new treatment plan or P block are shown in the steps of the flow chart in FIG. 6. As in the steps in creating new S, O, and A blocks, the user would select a note using the PN index 105. The process is initiated by the user from the PN window by selecting menu option P:Order 204. This action displays the order screen 205. This, in turn, calls the control layer 202. Here, the user can select laboratory requests and prescriptions from a list. As with the creation of S, O and A blocks, the information entered, or selected, is verified at the control layer 202. After verification at the control layer is complete, the data object and block list 203 are updated and the Progress Note notebook 109 is updated.

Figure 7:
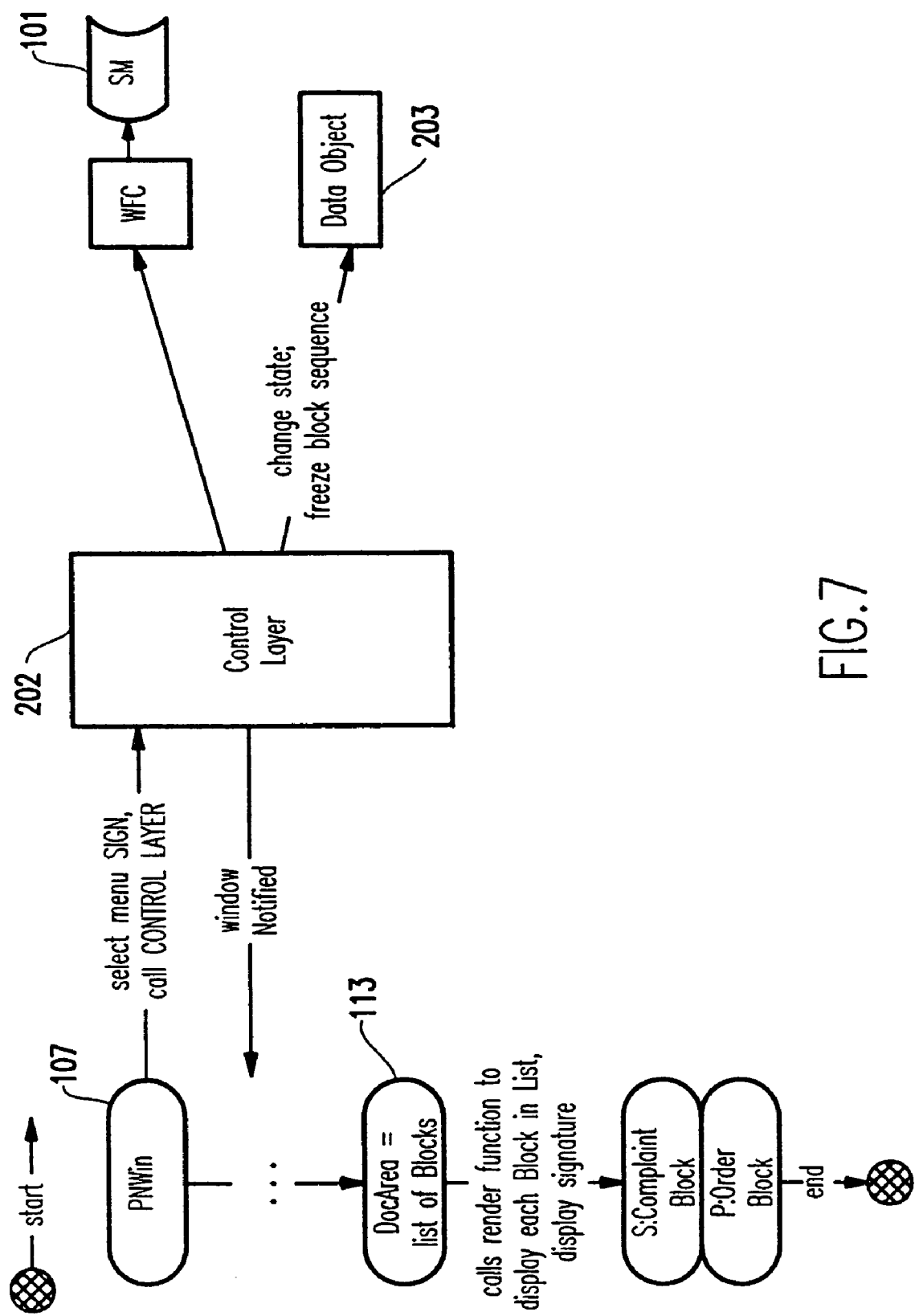
FIG. 7 is a flow chart, based on the flow chart of FIG. 1, showing the steps for signing or verifying a note.

FIG. 7 shows a flow chart of the steps of signing a note. A Progress Note will not be saved unless signed. After blocks are completed in the manner shown in the flow charts of FIGS. 5 and 6, the user must sign the note at the Progress Notes window 107. Again, the process is initiated from the PN Window 107 where the user selects from a displayed menu the action "SIGN". This calls the control layer 202. Signing is done by entry of a password known to the user. Once signed, the control layer 202 verifies the user's signature and compares it to the data entered by that user. When the signature is verified, the control layer 202 changes the status of the data object and block list 203 is frozen.

After a block has been created and signed it cannot be changed. However, a new version may be created. This enables the user to make corrections to data originally entered without deleting any of the data originally entered.

Two kinds of revisions are accommodated in the present invention: recording errors and revisions as an evolution or refinement of clinical judgement. When a version of a block is created, the newest version will always be displayed first with a notation that another version exists. The reader of the block will have the ability to toggle to review earlier versions of the block.

Figure 8:
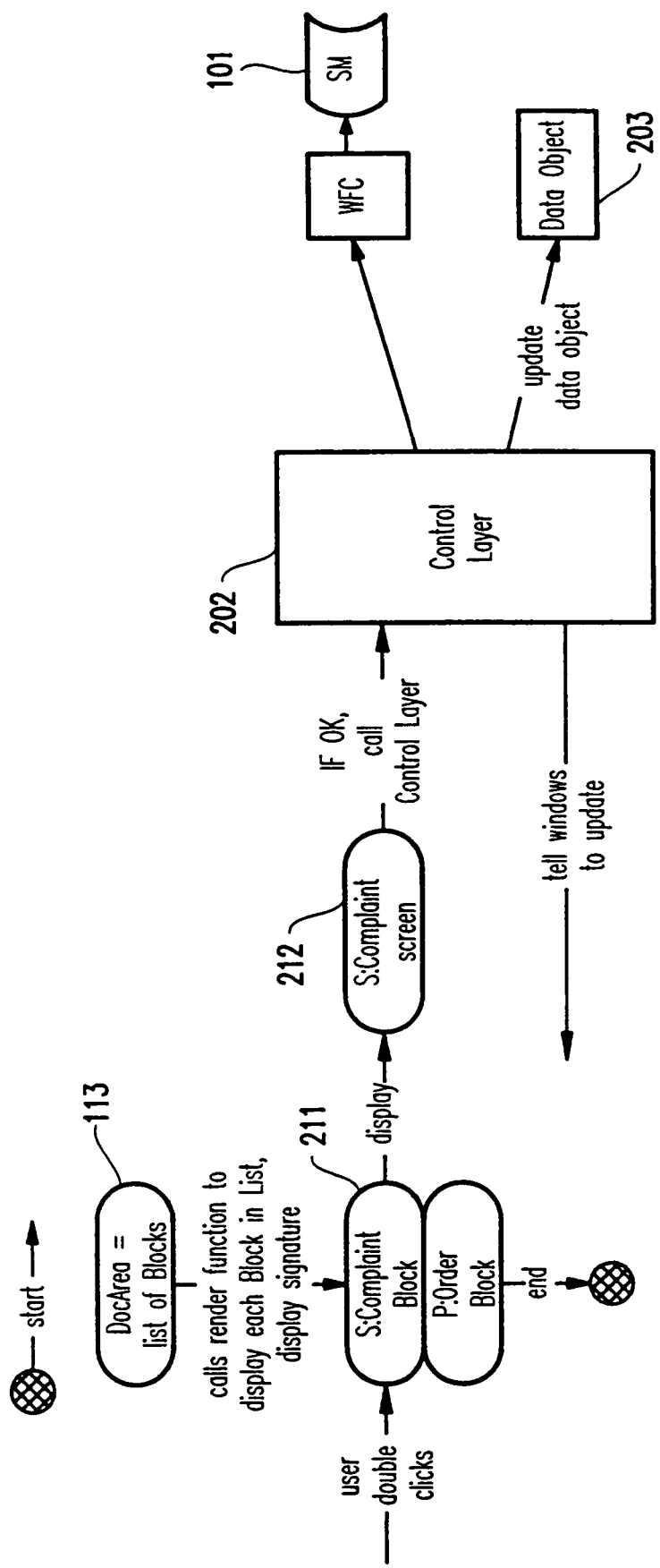
FIG. 8 is a flow chart, based on the flow chart of FIG. 1, showing the steps for revising a note.

The flow chart shown in FIG. 8 shows the steps of creating a version of an S block. From the document area 20 of a Progress Note page (see FIG. 2), the user first calls a render function to display each block in the list of blocks and also to display the signature attached to those blocks. Next, the user double clicks on the displayed S:Complaint block 211. This causes the S:Complaint screen 212 to be displayed. The user enters the new version of notes in the same screen as when the original version was created. Verifications are made in the control layer 202. Once verifications are made, the data object 203 is updated and the Progress Note window is updated.

Figure 9:
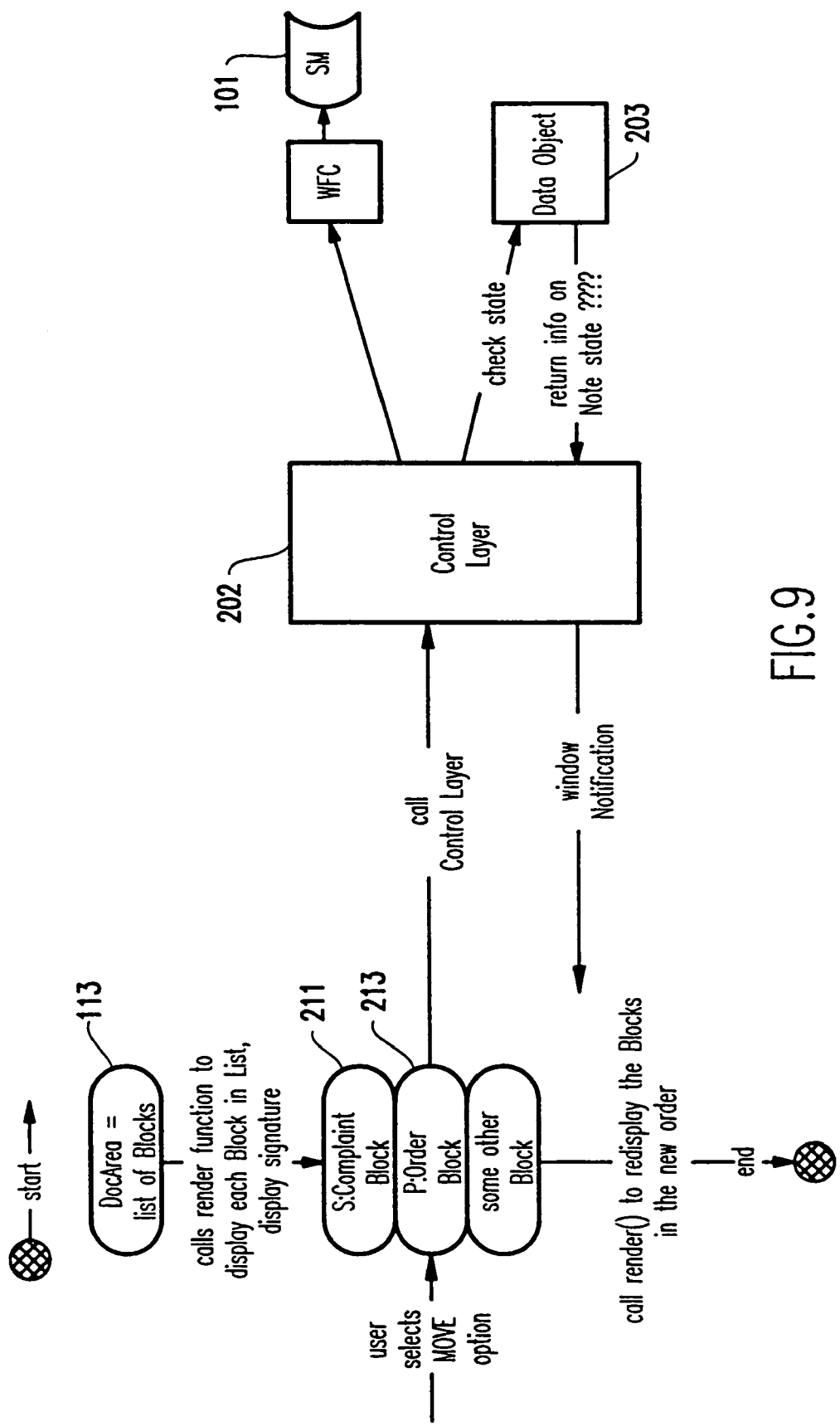
FIG. 9 is a flow chart, based on the flow chart of FIG. 1, showing the steps for moving blocks within a note.

The flow chart of FIG. 9 shows the steps of moving blocks. Again, the process is entered from the document area 20 (FIG. 2) where the user calls the render function to display each block in the list and also display the signature associated with the blocks. In this case, the user selects the "MOVE" option from a menu and clicks on the P:Order block 213. This action calls the control layer 202. the control layer 202 checks the state of the data object 203 and returns information to the PN Window to redisplay the blocks in the new order selected by the user.

FIG. 10 illustrates a portion of a sample progress note. Depicted in this note are:
1. Two committed P blocks: an order for a lab test 701, followed by a prescription 703.
2. Four baselet blocks: an S block 705 (Sore Throat), a reminder O block 707 (prompting to take the vital signs), an A block 709 (Acute Strep Throat), and a P block 711 (a prescription for Amoxicillin 500 mg).

The author of the note may choose to "keep," to "drop," or to change any one of the baselet blocks; e.g., there is no need to keep the baselet P block. Once it is determined which blocks to keep, and which to drop, blocks may be committed to the patient chart, e.g., by signing the note.

While the invention has been described in terms of a single preferred embodiment, those skilled in the art will recognize that the invention can be practiced with modification within the spirit and scope of the appended claims.

We claim:

1. A computer implemented method of creating a "baselet" for use in patient medical charts in a Clinical Information System (CIS), a "baselet" being a Progress Note (PN) in which coded elements from a knowledge base are pre-coordinated into a documentation template, the method comprising the steps of:
   accessing a library of baselets from a CIS database and creating an entry in the library for a new baselet;
   prompting via an input screen a care giver to input subjective information (S), objective data (0), an assessment (A), and a treatment plan (P) information into the baselet in a non-fixed format without storing the SOAP information in any individual patient medical chart in the CIS;
   prompting via an input screen the care giver to designate individual terms in the baselet as being in either a "positive", a "negative" or an "off" state; and
   storing the baselet, with all its terms and term state information, in the baselet library of a computer-based CIS; and
   editing or creating versions of the baselet for charting episodes of health care based on state of the stored baselet.

2. The computer implemented method of claim 1 further comprising the steps of:
   permitting the caregiver to modify the terms and term states of an existing baselet; and
   storing the modified baselet in the baselet library either as a new baselet or as a replacement for the original baselet.

3. A computer implemented method of creating a "baselet" for use in patient medical charts in a Clinical Information System (CIS) a "baselet" being a Progress Note (PN) in which coded elements from a knowledge base are pre-coordinated into a documentation template, the method comprising the steps of:
   accessing a library of baselets from a CIS database and creating an entry in the library for a new baselet;
   prompting via an input screen a care giver to input subjective information (S), objective data (0), an assessment (A), and a treatment plan (P) information into the baselet in a non-fixed format without storing the SOAP information in any individual patient medical chart in the CIS;
   prompting via an input screen the care giver to designate individual terms in the baselet as being in either a "positive", a "negative" or an "off" state; and storing the baselet, with all its terms and term state information, in the baselet library of a computer-based CIS;

editing or creating versions of the baselet for charting episodes of health care based on state of the stored baselet;

permitting the caregiver to place a baselet in a PN for a specific patient;

prompting the caregiver to apply to the PN in which the baselet has been placed only those terms from the baselet which are in the "positive" or "negative" states;

prompting the caregiver to input additional data as required by any term added to the PN; and storing the PN in the baselet library.

4. A computer implemented method of creating a "baselet" for use in patient medical charts in a Clinical Information System (CIS), a "baselet" being a Progress Note (PN) in which coded elements from a knowledge base are pre-coordinated into a documentation template, the method comprising the steps of:

accessing a library of baselets from a CIS database and creating an entry in the library for a new baselet;

prompting a care giver via an input screen to input subjective information (S), objective data (0), an assessment (A), and a treatment plan (P) information into the baselet without storing the SOAP information in any individual patient medical chart in the CIS;

prompting the care giver via the input screen to designate individual terms in the baselet as being in either a "positive", a "negative" or an "off" state;

storing the baselet, with all its terms and term state information, in the baselet library of a computer-based CIS, wherein the baselet includes providing for turning off completeness checking of data; and editing or creating versions of the baselet for charting episodes of health care based on the state of the stored baselet.

5. The method of claim 4, wherein the prompting step provides for inputting of the subjective information (S), the objective data (0), the assessment (A), and the treatment plan (P) information into the baselet in a non-fixed format.

* * * * *